(12) United States Patent
Shah

(10) Patent No.: US 7,708,716 B2
(45) Date of Patent: *May 4, 2010

(54) TREATMENT METHODS UTILIZING INFLATABLE DUAL BALLOON CATHETER

(76) Inventor: Tilak M. Shah, 104 Lochberry La., Cary, NC (US) 27511

( * ) Notice: Subject to any disclaimer, the term of this patent is extended or adjusted under 35 U.S.C. 154(b) by 305 days.

This patent is subject to a terminal disclaimer.

(21) Appl. No.: 11/748,940

(22) Filed: May 15, 2007

(65) Prior Publication Data

US 2007/0239110 A1    Oct. 11, 2007

Related U.S. Application Data

(63) Continuation of application No. 10/622,275, filed on Jul. 18, 2003, now Pat. No. 7,220,252.

(51) Int. Cl.
*A61M 31/00* (2006.01)
*A61M 29/00* (2006.01)

(52) U.S. Cl. .................. 604/101.02; 606/193

(58) Field of Classification Search ............. 604/96.01, 604/101.01, 101.02, 103.06, 103.07, 103.09; 606/191–193

See application file for complete search history.

(56) References Cited

U.S. PATENT DOCUMENTS

| | | |
|---|---|---|
| 3,173,418 A | 3/1965 | Baran |
| 4,338,942 A | 7/1982 | Fogarty |
| 4,668,224 A | 5/1987 | Lentz et al. |
| 4,994,033 A | 2/1991 | Shockey et al. |
| 5,512,051 A | 4/1996 | Wang et al. |
| 5,704,913 A | 1/1998 | Abele et al. |
| 5,865,801 A | 2/1999 | Houser |
| 5,868,776 A | 2/1999 | Wright |
| 6,102,929 A | 8/2000 | Conway et al. |
| 6,136,011 A | 10/2000 | Stambaugh |
| 6,156,053 A | 12/2000 | Gandhi et al. |
| 6,520,977 B2 | 2/2003 | Piraka |
| 6,676,680 B1 | 1/2004 | Packer |

(Continued)

OTHER PUBLICATIONS

Bakri, Y.N., et al., "Tamponade-balloon for obstetrical bleeding", "Int. J. Gynecol. Obstet.", Aug. 2001, pp. 139-142, vol. 74, No. 2.

(Continued)

*Primary Examiner*—Nicholas D Lucchesi
*Assistant Examiner*—Nathan R Price
(74) *Attorney, Agent, or Firm*—Vincent K. Gustafson; Intellectual/Property Technology Law

(57) ABSTRACT

A dual balloon catheter apparatus for controlling postpartum hemorrhage in uterine or vaginal cavities or hemorrhage in other body cavities, comprising: (1) a catheter having an inflation lumen and a deflation lumen; (2) a first inflatable balloon in fluid communication with the inflation lumen; and (3) a second inflatable balloon encompassing the first balloon and in fluid communication with the deflation lumen. A first fluid inflation medium can be introduced from an external fluid source through the inflation lumen to inflate the first balloon, so as to apply a substantially even pressure along a substantial portion of a uterine cavity to reduce or eliminate bleeding along such inner surface. The second inflatable balloon functions to confine any first fluid inflation medium that escapes (e.g., by leakage or rupture) from the first balloon, and to discharge such medium through the deflation lumen.

12 Claims, 5 Drawing Sheets

U.S. PATENT DOCUMENTS

| | | |
|---|---|---|
| 6,746,465 B2 | 6/2004 | Diederich et al. |
| 2003/0088209 A1 | 5/2003 | Chiu et al. |
| 2005/0015047 A1 | 1/2005 | Shah |

OTHER PUBLICATIONS

Condous, G.S., et al., "The 'Tamponade Test' in the Management of Massive Postpartum Hemorrhage", "Obstet. Gynecol.", Apr. 1, 2003, pp. 767-772, vol. 101, No. 4.

De Loor, Jeannette A., et al., "Foley catheters for uncontrollable obstetric or gynecologic hemorrhage", "Obstet. Gynecol.", Oct. 1, 1996, pp. 737, vol. 88, No. 4.

Goldrath, Milton H., et al., "Uterine tamponade for the control of acute uterine bleeding", "Am. J. Obstet. Gyncaecol.", Dec. 1983, pp. 869-872, vol. 147, No. 8.

Johanson, Richard, et al., "Management of massive postpartum haemorrhage: use of a hydrostatic balloon catheter to avoid laparotomy", "Br. J. Obstet. Gynaecol.", Apr. 2001, pp. 420-422, vol. 108, No. 4.

Jouppila, Pentti, "Postpartum haemorrhage", "Curr. Opin. Obstet. Gynecol.", 1995, pp. 446-450, vol. 7.

Katesmark, M., et al., "Successful use of a Sengstaken-Blakemore tube to control massive postpartum haemorrhage", "Br. J. Obstet. Gynaecol.", Mar. 1994, pp. 259-260, vol. 101, No. 3.

Kauff, Noah D., et al., "Intractable bleeding managed with Foley catheter tamponade after dilation and evacuation", "Am. J. Obstet. Gynecol.", Sep. 1995, pp. 957-958, vol. 173, No. 3 (pt 1).

Leoon, Fernando Garcia, et al., "Estado actual del taponamiento uterino con sonda de Foley en sangrado incoercible", "Ginecolgia y Obstetricia de Mexico", 1996, pp. 483-485, vol. 66.

Marcovici, Iacob, et al., "Postpartum hemorrhage and intrauterine balloon tamponade", "J. Reprod. Med.", Feb. 1999, pp. 122-126, vol. 44, No. 2.

Mousa, Hatem A., et al., "Major postpartum haemorrhage", "Curr. Opin. Obstet. Gynecol.", Dec. 2001, pp. 595-603, vol. 13, No. 6.

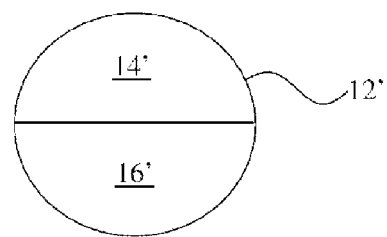
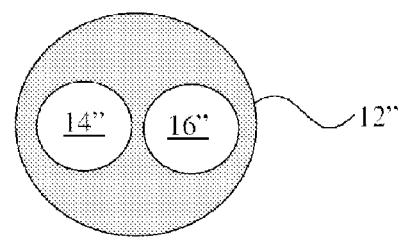
Figure 5A　　　　　　　　　　　Figure 5B
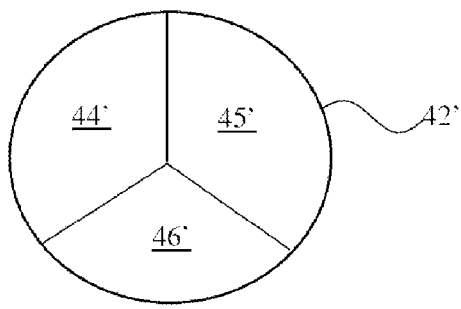
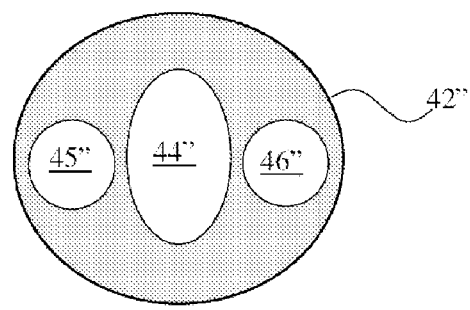
Figure 6A　　　　　　　　　　　Figure 6B

TREATMENT METHODS UTILIZING INFLATABLE DUAL BALLOON CATHETER

STATEMENT OF RELATED APPLICATIONS

This is a continuation of U.S. patent application Ser. No. 10/622,275 filed on Jul. 18, 2003 and entitled "Inflatable Dual Balloon Catheter."

FIELD OF THE INVENTION

This invention relates to an inflatable dual balloon catheter, and more particularly, to a dual balloon catheter used in conjunction with a tamponade device for controlling uterine and vaginal postpartum hemorrhage.

BACKGROUND OF THE INVENTION

Post-partum hemorrhage is most commonly caused by uterine atony whereby the uterus fails to contract normally after the delivery of a baby. This condition occurs in about 5 percent of deliveries. Hemorrhage continues to be one of the major causes of maternal deaths generally, with obstetrical hemorrhage being the third leading cause of maternal death by hemorrhage in the United States. Worldwide, maternal hemorrhage qualifies as the leading cause of maternal death.

Techniques for managing obstetrical hemorrhage may be medical, mechanical, or surgical. Hysterectomy, while an effective surgical procedure for treating this condition, bears severe consequences, in particular for young women who have not completed childbearing.

One of the mechanical procedures often used for managing obstetrical hemorrhage involves packing the uterus with heavy gauze. This procedure remains controversial because of a high failure rate, and is considered a waste of time by some medical practitioners. The high failure rate is attributable to the inherent difficulty in packing the uterus properly so that there is an even distribution of pressure along the entire inner surface of the organ.

Accordingly, a more effective procedure is needed to address post-partum hemorrhage and bleeding. Ideally, the procedure should present minimal long-term health consequences to the patient, be quickly and easily accomplished, be easily learned and require no specialized instrumentation.

U.S. Patent Application Publication No. US2001/0007945 published on Jul. 12, 2001 to Piraka, the contents of which are hereby incorporated by reference in their entirety for all purposes, discloses a uterine balloon for controlling hemorrhaging in a patient after childbirth. The balloon of Piraka is filled with a liquid medium, such as water or saline solution, by means of a catheter inserted through a valve in the balloon. A fill system, a control system, and a pressure relief valve are each employed for maintaining a constant solution pressure in the balloon. However, the pressure of the liquid medium is difficult to control and manage, especially when the balloon is only partially filled with such liquid medium. Further, weight of the liquid medium imposes additional pressure on the lower portion of the vaginal or uterine wall, which intensifies the discomfort of the patient during the procedure and may even result in injury of the soft tissues on the vaginal or uterine wall.

It is therefore an object of the present invention to provide a balloon catheter for controlling post-partum hemorrhage, with enhanced pressure control and reduced weight.

SUMMARY OF THE INVENTION

The present invention in one aspect relates to a dual balloon catheter that is inflatable by a gaseous inflation medium. Specifically, such balloon catheter comprises a first balloon, a second balloon that encompasses such first balloon, and a catheter having an inflation lumen and a deflation lumen that are separated from each other. The first balloon is in fluid communication with the inflation lumen of the catheter, and the second balloon is in fluid communication with the deflation lumen. After such dual balloon catheter is inserted into a body cavity, a biologically and physiologically compatible gaseous inflation medium, which includes but is not limited to, air, $O_2$, $N_2$, $Ar_2$, $CO_2$, etc., can be introduced through the inflation lumen to distend the first balloon inside the body cavity. The inflated first balloon applies a substantially even pressure along an inner surface of such body cavity, therefore reducing or eliminating bleeding alone such inner surface. The second balloon is not inflated but conforms to the contour of the first balloon. In the event that any gaseous inflation medium escapes from the first balloon, due to either leakage or rapture, such second balloon functions to confine the escaped gaseous medium and discharge it through the deflation lumen.

Therefore, the risk of gas embolism, which is caused by the entry of gas bubbles into the blood stream through hemorrhage sites and which may result in severe injury or even death, is significantly reduced by using the dual balloon catheter of the present invention. Moreover, the dual balloon catheter of the present invention, as inflated by a gaseous inflation medium, provides easy, accurate, and quick control of the pressure that is applied to the inner surface of a body cavity thereby. Further, the weight of the gas-inflated balloon of the present invention is significantly less than that of the liquid-inflated balloon disclosed by Piraka in U.S. Patent Application Publication No. US2001/0007945, therefore substantially reducing the discomfort of the patient and avoiding injury to the soft tissue on the inner surface of the body cavity.

Such dual balloon catheter can be inserted into a body cavity, such as uterine cavity, vaginal cavity, oral cavity, nasal cavity, cranial cavity, vertebral cavity, thoracic cavity, mediastinum, abdominal cavity, etc., for controlling bleeding therein. Alternatively, such dual balloon catheter can be used for dilating blood vessels to treat certain types of obstructions or occlusions therein. The contour of the balloons used depends on the specific shape of the body cavity to which the dual balloon catheter is inserted. For instance, when such dual balloon catheter is inserted into a uterine cavity, the first and second balloons are characterized by a heart-shaped contour that conforms to the inner surface of the uterine cavity; when such dual balloon catheter is inserted into a blood vessel, the first and second balloons are characterized by an elongated, tubular contour that conforms to the inner surface of the blood vessel. Conformance of the contour of the balloons with the interior shape of the body cavity enables such balloons to fit evenly and tightly against the inner surface of the body cavity, thereby providing pressure against all associated bleeding sites.

Such gas-inflated dual balloon catheter may further comprise a drainage/irrigation lumen in the catheter, which is isolated from the inflation and deflation lumens and which extends beyond the first and second balloons. The drainage/ irrigation lumen comprises a first open end and a second, opposite open end for draining blood or other body fluid from and/or injecting a cleaning or therapeutic fluid into the body cavity.

Another aspect of the present invention relates to a dual balloon catheter that is inflatable by a gaseous medium and a liquid medium. Specifically, such balloon catheter comprises a first balloon, a second balloon that encompasses such first balloon, and a catheter having a gas lumen and a liquid lumen that are separated from each other. The first balloon is in fluid communication with the gas lumen of the catheter, and the second balloon is in fluid communication with the liquid lumen. After such dual balloon catheter is inserted into a body cavity, a biologically and physiologically compatible gaseous medium, which includes but is not limited to air, $O_2$, $N_2$, $Ar_2$, $CO_2$, etc., can be introduced through the gas lumen to distend the first balloon, and a biologically and physiologically compatible liquid medium, such as water and saline solution, can be introduced through the liquid lumen to distend the second balloon. The inflated first and second balloons jointly apply a substantially even pressure along an inner surface of such body cavity, therefore reducing or eliminating bleeding alone such inner surface. In the event that any gaseous inflation medium escapes from the first balloon, due to either leakage or rapture, such second balloon functions to confine the escaped gaseous medium therein.

Therefore, the risk of gas embolism, which is caused by the entry of gas bubbles into the blood stream through hemorrhage sites and which may result in severe injury or even death, can be significantly reduced by using such dual balloon catheter of the present invention. Moreover, use of the gaseous medium in inflating the first balloon significantly reduces the overall weight of the gas/liquid-inflated dual balloon catheter, and therefore reducing the discomfort of the patient and avoiding injury to the soft tissue on the inner surface of the body cavity.

A further aspect of the present invention relates to a method of controlling post-partum hemorrhage, by using the gas-inflatable or the gas/liquid-inflatable dual balloon catheter described hereinabove.

Various other aspects, features and embodiments of the invention will be more fully apparent from the ensuing disclosure and claims.

BRIEF DESCRIPTION OF THE DRAWINGS

A more complex understanding of the invention may be obtained by reading the following description of specific illustrative embodiments of the invention in conjunction with the appended drawing in which:

FIGS. 5A and 5B show transversal cross-section views of catheter tubes of gas-inflated dual balloon catheter apparatuses having non-concentric inflation and deflation lumens.

FIGS. 6A and 6B show transversal cross-section views of catheter tubes of gas-inflated dual balloon catheter apparatuses having non-concentric inflation, deflation, and drainage/irrigation lumens.

DETAILED DESCRIPTION OF THE PREFERRED EMBODIMENTS

The following detailed description includes a description of the preferred embodiments of the invention presently contemplated. Such description is not intended to be understood in a limiting sense, but to be an example of the invention presented solely for illustration thereof, and by reference to which in connection with the following description and the accompanying drawing one skilled in the art may be advised of the advantages and construction of the invention.

Figure 1:
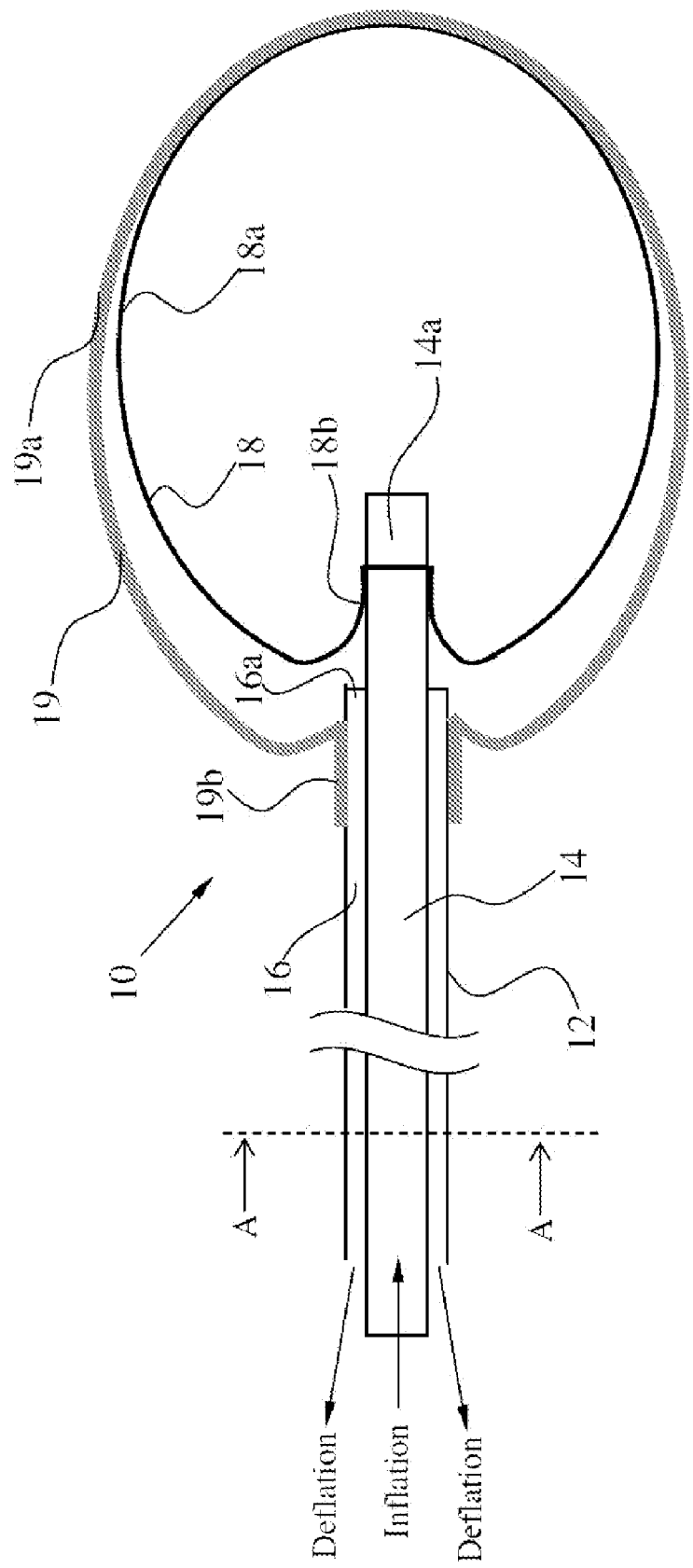
FIG. 1 shows a longitudinal cross-sectional view of a gas-inflated dual balloon catheter apparatus, according to one embodiment of the present invention.

Referring to the FIG. 1, a dual balloon catheter apparatus 10 comprises a first, inner balloon 18, a second, outer balloon 19, and a catheter 12. The catheter has an inflation lumen 14 and a deflation lumen 16 that are isolated from each other. Opening 14a of the inflation lumen 14 extends beyond opening 16a of the deflation lumen 16 into the first, inner balloon 18. The first, inner balloon 18 comprises an inflatable portion 18a and a neck portion 18b that is leak-tightly engaged with the catheter at a location that is adjacent to the opening 14a of the inflation lumen 14. A gaseous inflation medium, such as air, $O_2$, $N_2$, $Ar_2$, $CO_2$, etc., can be introduced into the first, inner balloon 18 from the inflation lumen to distend the first balloon 18. Opening 16a of the deflation lumen 16 extends into the second, outer balloon 19, which comprises an inflatable portion 19a and a neck portion 19b that is leak-tightly engaged with the catheter at a location that is adjacent to the opening 16a.

For controlling post-partum hemorrhage, a flat dual balloon catheter apparatus 10 is inserted into the uterine cavity of a patient. A gaseous inflation medium as described hereinabove from an inflation gas source is introduced into the first, inner balloon 18 through the inflation lumen 14, so as to distend the first balloon 18 and to apply a substantially even pressure to a substantial portion of an inner surface of the uterine cavity. Such pressure can effectively reduce or eliminate bleeding along such inner surface of the uterine cavity, therefore.

During such process, the second, outer balloon 19 is not inflated, but conforms to the contour of the inflated inner balloon 18 instead. The function of such second, outer balloon 19 is to confine any gaseous inflation medium that escapes from the first, inner balloon 18, due to either leakage or rapture of such first balloon 18, and to discharge the escaped gaseous inflation medium through the deflation lumen into the atmosphere or a subatmospheric environment (such as a vacuum), therefore reducing the risk of gas embolism caused by entry of gas bubbles into the blood stream through hemorrhage sites.

The weight of the gas-inflated dual balloon catheter apparatus 10 is minimum, in comparison to the liquid-inflated balloon catheter disclosed by Piraka in U.S. Patent Application Publication No. US2001/0007945, therefore reducing the discomfort of the patient during the treatment process.

The inflation lumen 14 preferably mates with one or more inflation and/or pressure control valves (not shown) for maintaining the inner balloon 18 in an inflated state, and for controllably deflating the inner balloon 18 when it is required that pressure supplied to the uterine cavity be reduced or altogether removed. Such inflation and/or pressure control valves may comprise a variety of conventional devices including, for example, ball valves and needle valves.

The first and the second balloons 18 and 19 are preferably, but not necessarily, arranged in a substantially concentric relationship, i.e., the distance between the centers of such first and second balloons are minimum in light of their overall diameters.

Figure 3:
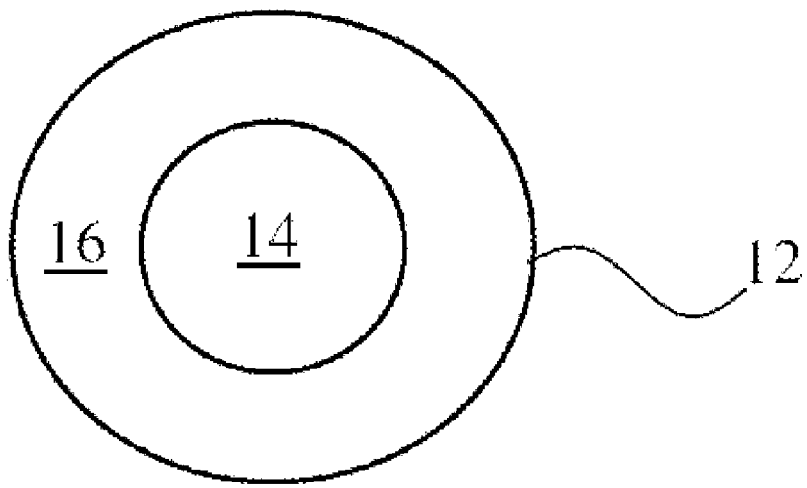
FIG. 3 shows a transversal cross-sectional view of the catheter tube of the gas-inflated dual balloon catheter apparatus of FIG. 1, along line A-A.

The inflation and deflation lumens 14 and 16 of the catheter 12 are preferably concentric, as shown in FIG. 3, wherein the deflation lumen 16 preferably circumscribes the inflation lumen 14. Alternatively, the inflation and deflation lumens of the catheter are not concentric, as shown in FIGS. 5A and 5B. The shape and configuration of the inflation and deflation lumens as shown in FIGS. 3 and 5A-5B are provided only for illustration purposes, and should not be construed to limit the broad scope of the present invention.

Balloons 18 and 19 are made of one or more elastomic or elastoplastic polymeric materials, such as silicone, urethanes, latex, ethylene vinyl acetate (EVA), polyisoprene, styrenic elastomer, polyvinyl chloride, polyamide elastomer, polyester elastomer, polytetrafluoro elastomer, polyamide elastoplastic, polyester elastoplastic, etc., and mixtures thereof. Additional fillers and additives can be provided for enhancing the properties of such polymeric materials. Balloons 18 and 19 may be made of the same or different polymeric materials.

Further, an external surface of the inner balloon 18 may be coated with a friction-reducing material, such as a lubricant, to reduce the coefficient of friction (COF) between such external surface of the inner balloon 18 and an inner surface of the outer balloon 19.

Moreover, an external surface of the outer balloon 19 may preferably be coated, impregnated or otherwise covered with a therapeutic agent, such as an anti-microbial or a hormone, for delivery thereof, or a hemostatic material, such as oxidized cellulose and hemotene, for contact with the inner surface of the body cavity to further assist in controlling bleeding.

Figure 2:
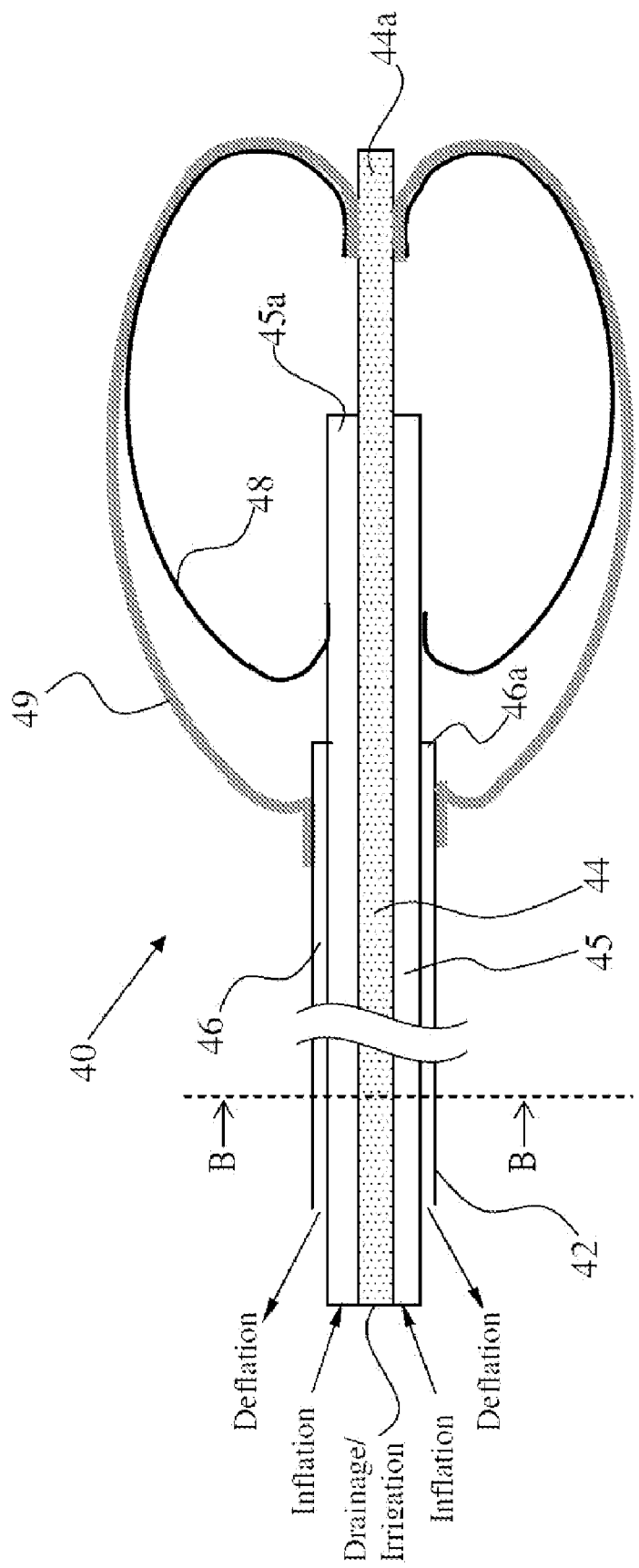
FIG. 2 shows a longitudinal cross-sectional view of a gas-inflated dual balloon catheter apparatus having a drainage/irrigation lumen, according to one embodiment of the present invention.

FIG. 2 shows a dual balloon catheter 40 comprising a first, inner balloon 48, a second, outer balloon 49, and a catheter 42. The catheter 42 specifically comprises: (1) an inflation lumen 45 having an opening 45a into the first, inner balloon 48, (2) a deflation lumen 46 having an opening 46a into the second, outer balloon 49, and (3) a drainage/irrigation lumen 44 that extends beyond the inner and outer balloons 48 and 49. Such drainage/irrigation lumen 44 has a first open end (labeled as "drainage") and a second, opposite open end 44a. When the dual balloon catheter 40 is inserted into a body cavity, the drainage/irrigation lumen functions to drain blood or other body fluid from such body cavity, or to inject a cleaning or therapeutic solution into such body cavity, for cleansing or treatment thereof.

Both the first and second balloons 48 and 49 comprise an inflatable portion, a first neck portion (left) and a second neck portion (right). The first neck portions (left) of such first and second balloons 48 and 49 are leak-tightly engaged with the catheter at respective locations so as to ensure fluid communication of the first balloon 48 with the inflation lumen 45 and (2) the second balloon 49 with the deflation lumen 46. The second neck portions (right) of such first and second balloons 48 and 49 are leak-tightly engaged with the catheter at a location adjacent to the second, opposite open end 44a of the drainage/irrigation lumen 44, so that the drainage/irrigation lumen 44 opens to the exterior instead of the interior of the first and second balloons 48 and 49, as shown in FIG. 2.

Figure 4:
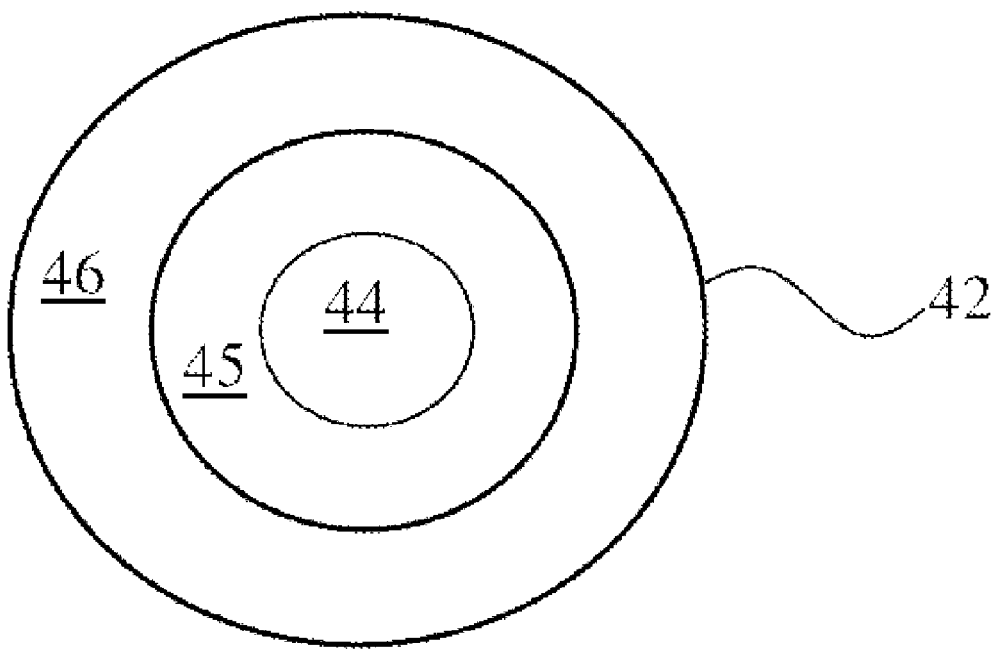
FIG. 4 shows a transversal cross-sectional view of the catheter tube of the gas-inflated dual balloon catheter apparatus of FIG. 3, along line B-B.

The inflation, deflation, and drainage/irrigation lumens 44, 45, and 46 of the catheter 42 are preferably concentric, as shown in FIG. 4, wherein the deflation lumen 46 preferably circumscribes the inflation lumen 45, which in turn circumscribes the drainage/irrigation lumen 44. Alternatively, the inflation, deflation, and drainage/irrigation lumens 44, 45, and 46 of the catheter 42 are not concentric, as shown in FIGS. 6A and 6B. The shape and configurations of the inflation, deflation, and drainage/irrigation lumens as shown in FIGS. 4 and 6A-6B are provided only for illustration purposes, and should not be construed to limit the broad scope of the present invention.

The above-described dual balloon catheters 10 and 40 are inflated by a gaseous inflation medium, which minimizes the weight of the inflated balloon catheter and reduces discomfort of the patient caused by the additional pressure applied to the inner wall of the body cavity by such weight.

Alternatively, the dual balloon catheter can be partially inflated by a gaseous inflation medium, i.e., in the first, inner balloon, and the remaining volume of such dual balloon catheter, i.e., in the second, outer balloon, can be inflated by a liquid inflation medium such as water or saline solution. Use of the gaseous inflation medium substantially reduces the overall weight of the inflated balloon catheter, in comparison with that of a balloon catheter that is completely inflated by a liquid, while at the same time, the liquid inflation medium can be used to heat or cool the inner surface of the body cavity for treatment thereof.

Figure 7:
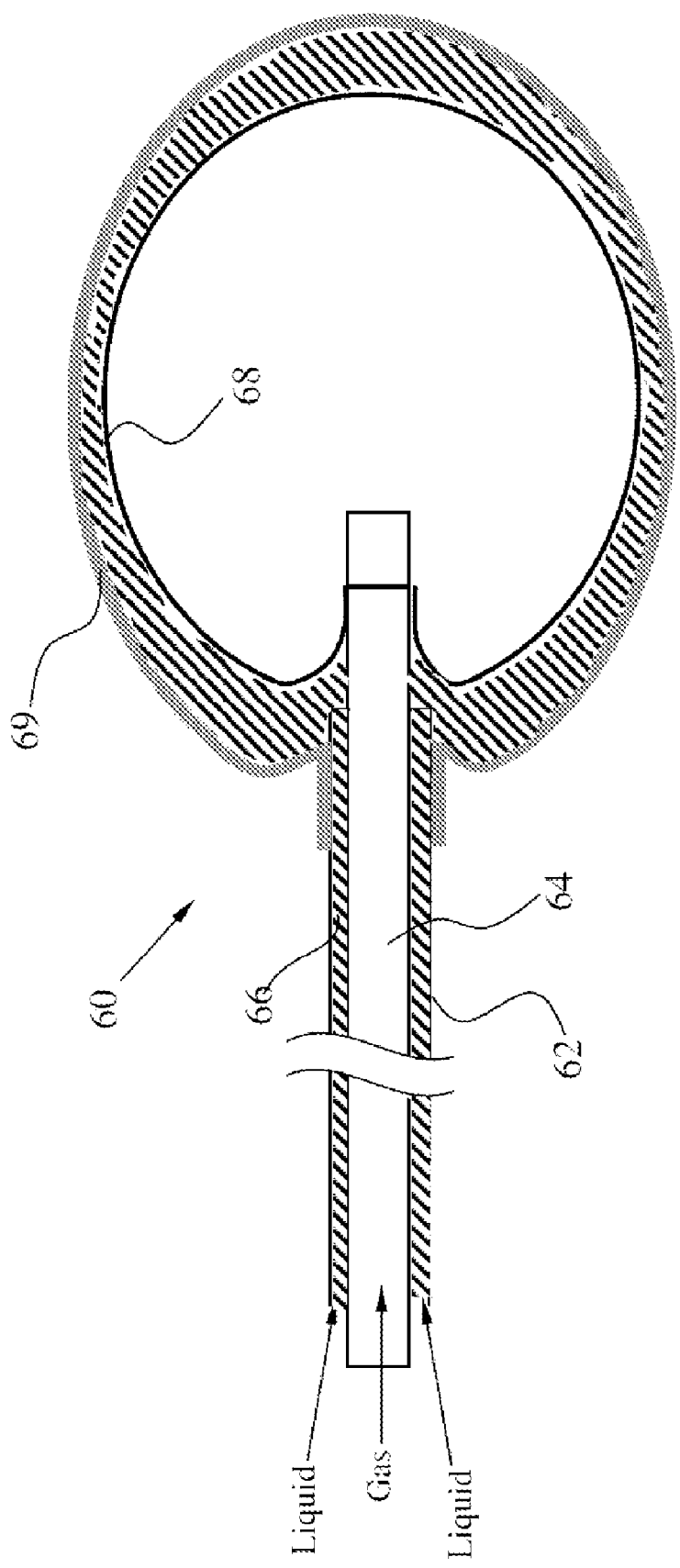
FIG. 7 shows a longitudinal cross-sectional view of a gas/liquid-inflated dual balloon catheter apparatus, according to one embodiment of the present invention.

FIG. 7 shows a gas/liquid-inflated dual balloon catheter apparatus 60 that is similar to the gas-inflated dual balloon catheter 10 of FIG. 1, except that the catheter 62 of such apparatus 60 comprises (1) a gas lumen 64 that opens into the first, inner balloon 68, for inflating such inner balloon 68 with a gaseous inflation medium, and (2) a liquid lumen 66 that opens into the second, outer balloon 69, for inflating such outer balloon 69 with a liquid inflation medium.

The volumetric ratio between the inner and outer balloons 68 and 69 (i.e., the volumetric ratio between gas and liquid medium) is preferably in a range of from about 1:1 to about 1000:1.

Such gas/liquid-inflated dual balloon catheter apparatus 60 may further comprise a drainage/irrigation lumen (not shown) circumvented by the gas lumen 64 and liquid lumen 66, which extends beyond the first and second balloons 68 and 69 for draining body fluids from, or injecting cleaning or therapeutic solutions into, the body cavity.

The gas-inflated or gas/liquid-inflated dual balloon catheter apparatus of the present invention may be simply operated by inserting such apparatus to a desired position in a body cavity such as a uterine cavity, and inflating the first, inner balloon and/or the second, outer balloon to a desired pressure and volume. Optimum pressure is detected, for example, when there is no further fluid drainage. After an appropriate length of time, pressure can be lowered and observations made to determine whether or not bleeding has been controlled. If bleeding begins again, the balloon may be reinflated.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

What is claimed is:

1. A method for controlling post-partum hemorrhage, the method comprising:

providing a balloon catheter apparatus comprising:
- a catheter having at least two lumens that are isolated from each other, one of which being an inflation lumen, and the other of which being a deflation lumen;
- a first balloon having an inflatable portion and at least one neck portion, wherein said first balloon is in fluid communication with the inflation lumen, so that a fluid inflation medium can be introduced into said first balloon through the inflation lumen; and
- a second balloon encompassing said first balloon, wherein said second balloon has an inflatable portion and at least one neck portion, and wherein said second balloon is in fluid communication with the deflation lumen, so that any fluid inflation medium in said second balloon can be discharged from said second balloon through the deflation lumen;
- wherein at least one of the first balloon and the second balloon comprises an elastomic or elastoplastic polymeric material;

inserting the balloon catheter apparatus into at least one of an internal uterine wall area and a vaginal wall area; and inflating the first balloon with a first fluid inflation medium so as to apply a substantially even pressure over the at least one of an internal uterine wall area and a vaginal wall area for reducing or eliminating bleeding therein.

2. The method of claim 1, wherein said elastomic or elastoplastic material comprises any of: silicone, urethane, latex, ethylene vinyl acetate (EVA), polyisoprene, styrenic elastomer, polyvinyl chloride, polyamide elastomer, polyester elastomer, polytetrafluoro elastomer, polyamide elastoplastic, and polyester elastoplastic.

3. The method of claim 1, wherein the second balloon is coated with a hemostatic material adapted to moderate or reduce hemorrhage of the at least one of an internal uterine wall area and a vaginal wall area.

4. The method of claim 3, wherein the hemostatic material comprises oxidized cellulose.

5. The method of claim 3, wherein the hemostatic material comprises hemotene.

6. The method of claim 1, wherein at least a portion of each of the first balloon and the second balloon is shaped to conform to the inner surface of a uterine cavity.

7. The method of claim 1, wherein at least a portion of each of the first balloon and the second balloon is substantially heart-shaped.

8. The method of claim 1, further comprising inflating the second balloon with a second fluid inflation medium.

9. The method of claim 8, further comprising heating the second fluid inflation medium.

10. The method of claim 8, further comprising cooling the second fluid inflation medium.

11. The method of claim 10, further comprising controllably deflating any of the first balloon and the second balloon.

12. The method of claim 1, wherein the balloon catheter apparatus further includes a lumen adapted for any of drainage and irrigation, and the method further comprises any of: (a) extracting or draining body fluid from any of a uterine area and a vaginal area, (b) supplying cleaning fluid into any of a uterine area and a vaginal area, and (c) supplying therapeutic fluid into any of a uterine area and a vaginal area.

* * * * *